United States Patent
Yoon et al.

(10) Patent No.: US 12,305,097 B2
(45) Date of Patent: May 20, 2025

(54) FLUORESCENT SILICA NANOPARTICLES USING SILANE-LANTHANUM-BASE COMPLEX COMPOSITE AND CROSS-LINKING REACTION AND METHOD FOR MANUFACTURING SAME

(71) Applicant: AJOU UNIVERSITY INDUSTRY-ACADEMIC COOPERATION FOUNDATION, Suwon-si (KR)

(72) Inventors: Hyun C. Yoon, Seoul (KR); Ka Ram Kim, Suwon-si (KR); Yong Duk Han, Seongnam-si (KR); Yoo Min Park, Seoul (KR); Hyeong Jin Chun, Anyang-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 744 days.

(21) Appl. No.: 15/999,776

(22) PCT Filed: Feb. 14, 2017

(86) PCT No.: PCT/KR2017/001604
§ 371 (c)(1),
(2) Date: Aug. 20, 2018

(87) PCT Pub. No.: WO2017/142289
PCT Pub. Date: Aug. 24, 2017

(65) Prior Publication Data
US 2021/0002546 A1    Jan. 7, 2021

(30) Foreign Application Priority Data
Feb. 18, 2016 (KR) .......... 10-2016-0019392

(51) Int. Cl.
*C09K 11/06* (2006.01)
*B82Y 40/00* (2011.01)
(Continued)

(52) U.S. Cl.
CPC .............. *C09K 11/06* (2013.01); *C01B 33/18* (2013.01); *C09K 11/025* (2013.01); *C09K 11/77* (2013.01);
(Continued)

(58) Field of Classification Search
CPC . C09K 11/06; C09K 11/025; C09K 2211/182; C01B 33/18; G01N 33/533
See application file for complete search history.

(56) References Cited

U.S. PATENT DOCUMENTS 8,268,355 B2 * 9/2012 Raccurt .............. H01L 51/5012
424/489

OTHER PUBLICATIONS

Wu et al, "Visile-light-sensitized highly luminescent europium nanoparticles: preparation and application for time-gated luminescence bioimaging", Journal of Materials Chemistry, vol. 19, Jan. 22, 2009, pp. 1258-1264.*
(Continued)

*Primary Examiner* — C Melissa Koslow
(74) *Attorney, Agent, or Firm* — Vorys, Sater, Seymour and Pease LLP; Mih Suhn Koh

(57) ABSTRACT

Disclosed is a method of manufacturing lanthanide fluorescent silica nanoparticles, including a complex synthesis step of synthesizing a silane-lanthanide chelate complex, an emulsion formation step of forming a water-in-oil microemulsion by dispersing micelles, the water-phase core of which is introduced with the silane-lanthanide chelate complex, in an oil-phase solvent, a silica introduction step of introducing a silica precursor into the microemulsion, and a nanoparticle synthesis step of synthesizing fluorescent silica (Continued)

nanoparticles by crosslinking the silica precursor and the silane-lanthanide chelate complex in the micelles. The lanthanide fluorescent silica nanoparticles thus manufactured can be utilized in fluorescence analysis of inorganic materials or bio-derived materials.

17 Claims, 7 Drawing Sheets

(51) Int. Cl.
 *C01B 33/18* (2006.01)
 *C09K 11/02* (2006.01)
 *C09K 11/77* (2006.01)
 *G01N 33/533* (2006.01)
(52) U.S. Cl.
 CPC ............ *G01N 33/533* (2013.01); *B82Y 40/00* (2013.01); *C09K 2211/182* (2013.01)

(56) References Cited

OTHER PUBLICATIONS

Park et al, "Effect of Alcohol Chain Length on Particle Growth in a Mixed Solvent System", Jornal of Ceramic Processing Research, vol. 7, No. 1, pp. 83-89, 2006.*

* cited by examiner

[FIG. 1]
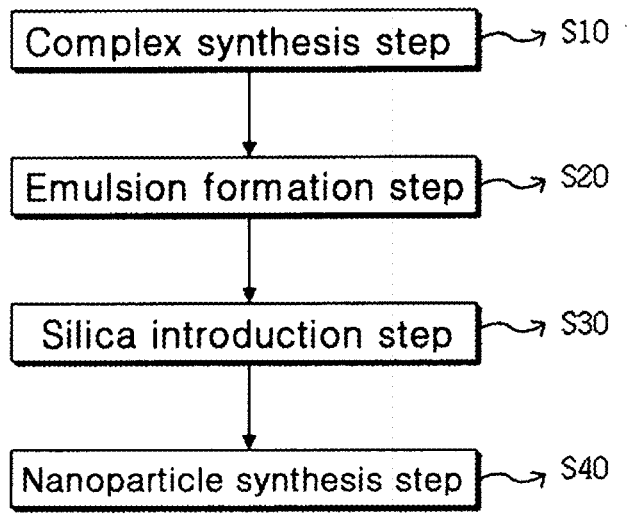
[FIG. 2]
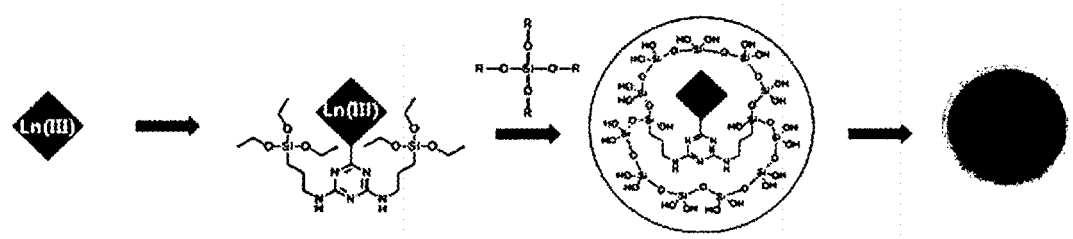

[FIG. 3]
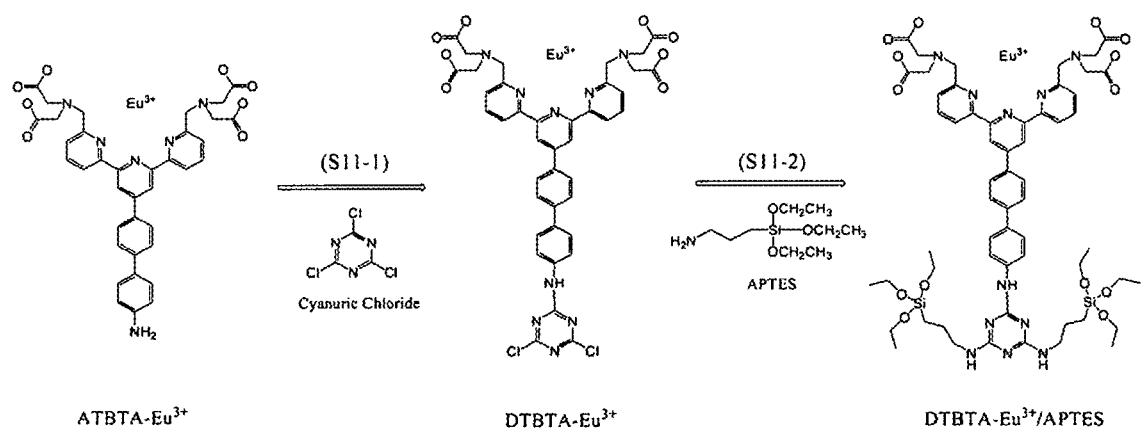
[FIG. 4]
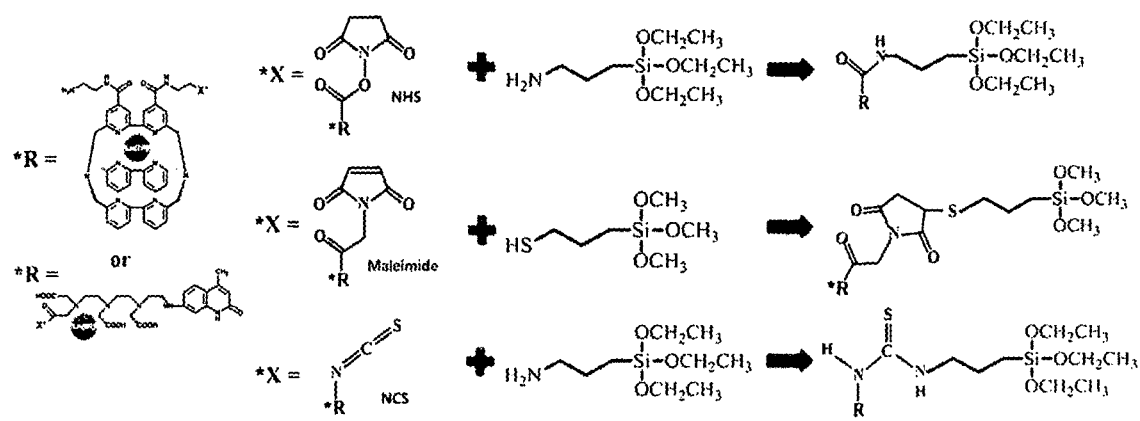

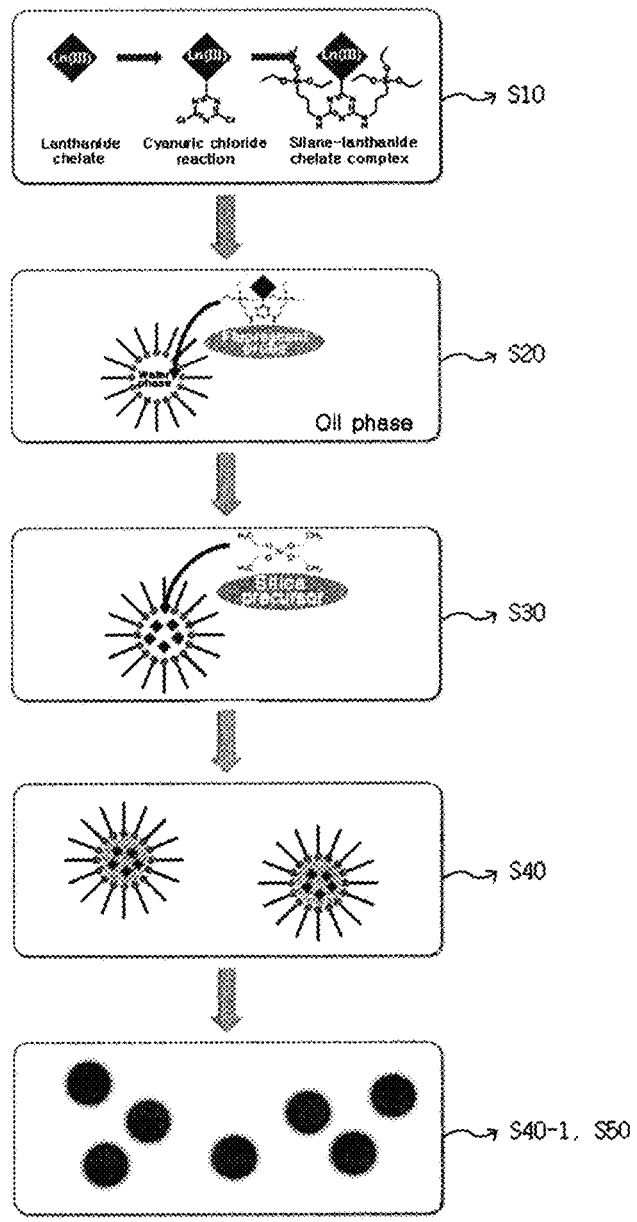
[FIG. 5]

[FIG. 6]
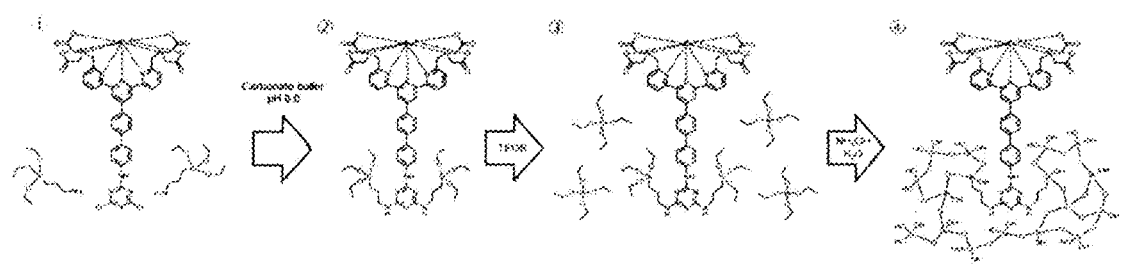
[FIG. 7]
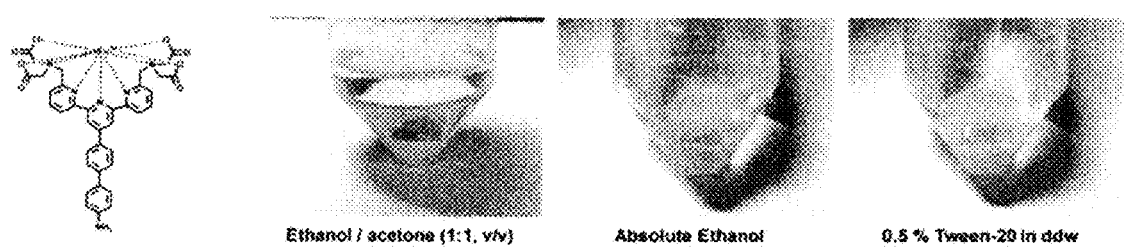
[FIG. 8]
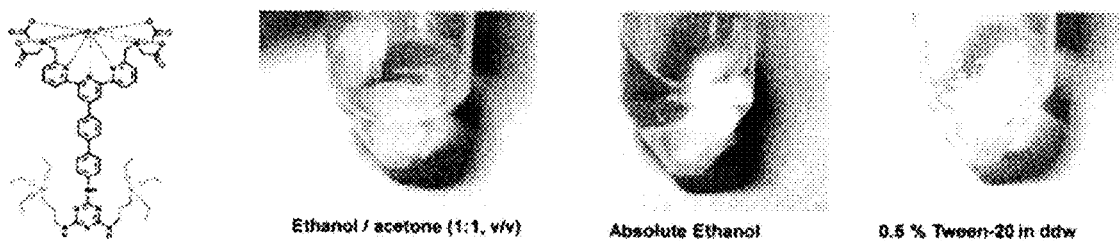

[FIG. 9]
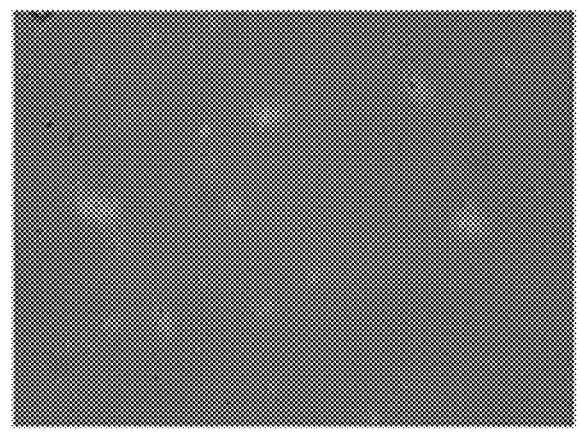
[FIG. 10]
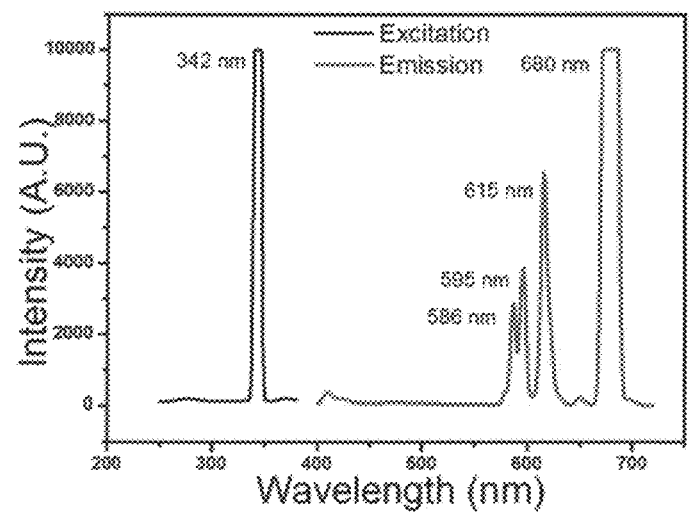

[FIG. 11]
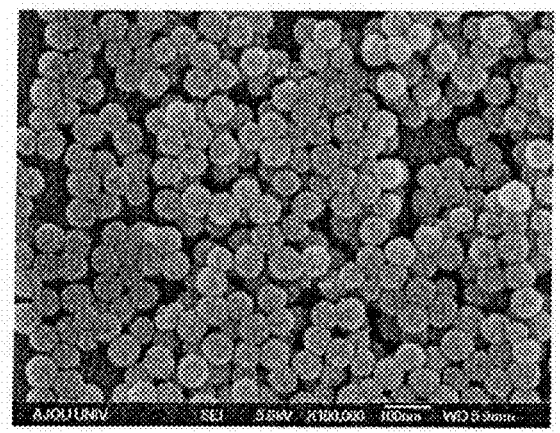
[FIG. 12]
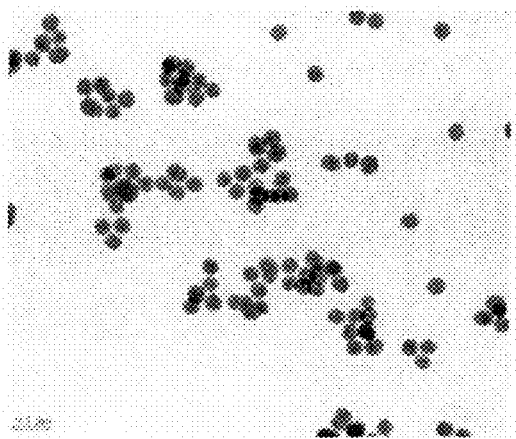

[FIG. 13]
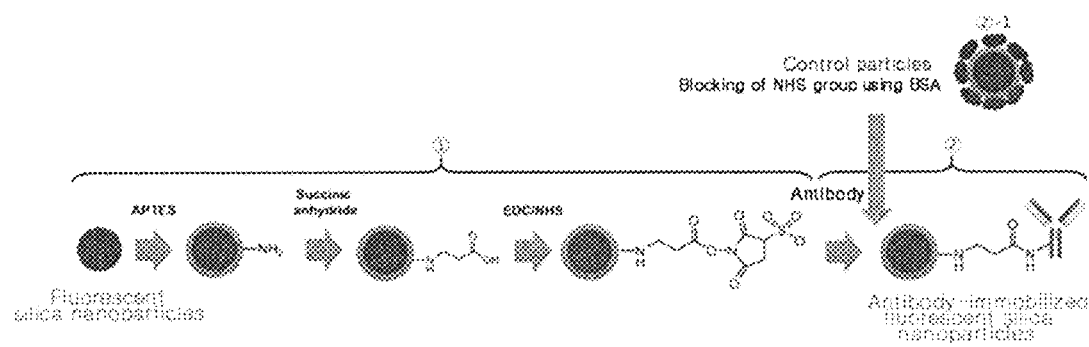
[FIG. 14]
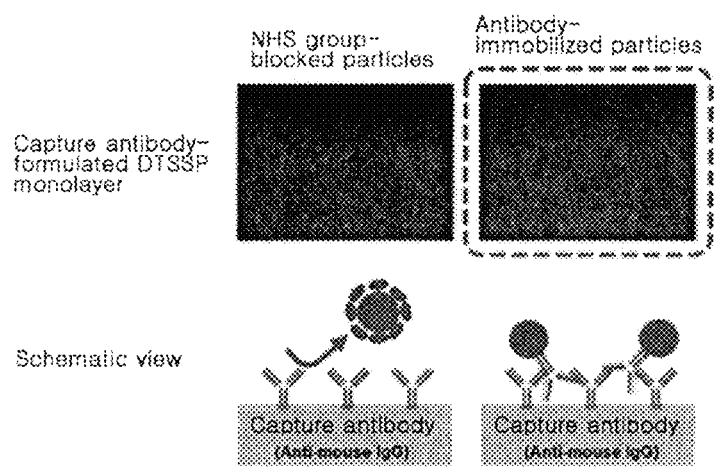

FLUORESCENT SILICA NANOPARTICLES USING SILANE-LANTHANUM-BASE COMPLEX COMPOSITE AND CROSS-LINKING REACTION AND METHOD FOR MANUFACTURING SAME

TECHNICAL FIELD

The present invention relates to fluorescent silica nanoparticles using a silane-lanthanide chelate complex and a crosslinking reaction and a method of manufacturing the same, and more particularly to fluorescent silica nanoparticles suitable for use in fluorescence analysis of inorganic materials or bio-derived materials.

BACKGROUND ART

Biotechnology is currently converging with many other disciplines and technologies and has effectively broadened to encompass a variety of fields. In particular, thorough research into biomaterial analysis and detection markets is ongoing. Methods for use in biomaterial analysis and measurement involve the attachment of a biomaterial to the surface of microparticles or nanoparticles using nanoparticles or beads.

A fluorescence assay, which is utilized as a bio-derived material measurement method (molecular-level diagnosis), is a method of quantitative/qualitative analysis of a target material through measurement of fluorescence signal intensity of a fluorescent probe that reacts with the target material. As the fluorescent probe, which emits a fluorescence signal, various kinds of materials including organic compounds, metal nanoparticles and proteins are used, and new kinds of materials therefor are being developed. Useful as a promising material for biomaterial diagnosis and measurement techniques are fluorescent nanoparticles obtained by introducing a fluorescent material into silica nanoparticles having a large surface area and pores.

Mesoporous silica nanoparticles (MSN) having a pore size of 2 to 50 nm are regarded as important nanomaterials having numerous applications in the fields of catalysts, adsorbents, polymeric fillers, optical devices, bio-imaging materials, drug delivery agents, and biomedicines.

Since MSN exhibits properties that vary depending on the shape, size, uniformity and dispersivity thereof, the synthesis of MSN, the meso structure of which is variously adjusted in the size range from ones of nm to hundreds of nm in the aforementioned application fields, has been a very important research topic, and various synthesis principles have been developed to date.

Typical examples thereof may include a synthesis method using fast self-assembly, a synthesis method using a soft template and a hard template, a modified Stöber method, a sol-gel method, etc.

Fluorescence assays are advantageous in that they have high signal sensitivity compared to other assay methods, as determined based on the fluorescence properties of a fluorescent material, and for successful signal measurement and analysis, a fluorescent material having a desired wavelength range suitable for the material to be measured is selected. Despite these advantages, however, many materials that cause an auto-fluorescence phenomenon other than the signal of the fluorescent probe bound to the target material are present in bio-derived materials, and interfere with the fluorescence signal emitted by the fluorescent probe, thus hindering the acquisition of a target-specific signal and thereby deteriorating the sensitivity of the fluorescence signal.

Thus, in order to perform measurement of a material that requires high sensitivity compared to a conventionally commercially available diagnostic target material, a probe that is not affected by the auto-fluorescence signal of the bio-derived material has to be used. Hence, nanoparticles using as a fluorescent material a lanthanide element having a long emission half-life due to a wide Stokes shift and chemical stability of a molecule have been researched and commercialized. However, the nanoparticles using a lanthanide element as a fluorescent probe for high-sensitivity molecular-level analysis have problems with respect to the manufacturing method thereof.

The nanoparticles, configured to include silica and polymer-based nanoparticles, which are most commonly used in the art, are typically problematic because any material contained therein may be lost to the outside of the particles. This is mainly caused by the porosity of the silica structure and the swelling of the polymer structure, and the fluorescent probe thus lost may not only contaminate a sample in the diagnosis-based analysis but also makes it difficult to obtain a binding signal specific to the target material. Furthermore, water and oxygen have to be blocked for the chemical stability of the fluorescent probe, but polymer-based nanoparticles are disadvantageous in that sufficient shielding effects are not exhibited due to swelling of the polymer structure.

Therefore, it is necessary to manufacture silica particles, which may minimize a reduction in sensitivity due to auto-fluorescence and may block external environmental factors in order to perform fluorescence analysis of a bio-derived material, particularly fluorescent silica nanoparticles, which may prevent the internal material from being lost to the outside of the particles due to the porous structure of silica.

DISCLOSURE

Technical Problem

Accordingly, the present invention has been made keeping in mind the problems in the related art, and an aspect of the present invention is to provide a method of manufacturing fluorescent silica nanoparticles by synthesizing a fluorescent probe complex having a novel structure and cross-linking the fluorescent probe complex with a silica structure.

In addition, another aspect of the present invention is to provide fluorescent silica nanoparticles, which may be utilized in fluorescence analysis of inorganic materials, bio-derived materials, or the like.

The aspects of the present invention are not limited to the foregoing, and other aspects which are not mentioned herein will be able to be clearly understood by those skilled in the art from the following description.

Technical Solution

The present invention provides a method of manufacturing lanthanide fluorescent silica nanoparticles, comprising: a complex synthesis step (S10) of synthesizing a silane-lanthanide chelate complex, an emulsion formation step (S20) of forming a water-in-oil microemulsion by dispersing micelles, the water-phase core of which is introduced with the silane-lanthanide chelate complex, in an oil-phase solvent, a silica introduction step (S30) of introducing a silica precursor into the microemulsion, and a nanoparticle synthesis step (S40) of synthesizing fluorescent silica nanoparticles by crosslinking the silica precursor and the silane-lanthanide chelate complex in the micelles.

The complex synthesis step (S10) is a complex synthesis step based on the first process, comprising: a first complex synthesis step (S11-1) of synthesizing a cyanuric chloride-lanthanide chelate by adding and reacting a lanthanide chelate (*R) containing an amine group with cyanuric chloride, and a second complex synthesis step (S11-2) of synthesizing a silane-lanthanide chelate complex by adding and reacting the cyanuric chloride-lanthanide chelate with aminosilane.

Alternatively, the complex synthesis step (S10) is a complex synthesis step (S12) based on the second process, comprising: synthesizing a silane-lanthanide chelate complex by adding and reacting a lanthanide chelate (*R) containing a residue (*X) having reactivity to an amine group or a thiol group with a silane compound having an amine group or a thiol group.

The residue (*X) includes at least one functional group selected from the group consisting of carboxylate, N-hydroxysuccinimide, isothiocyanate, maleimide and sulfonyl chloride.

The lanthanide chelate (*R) includes a TBP-Ln(III) chelate, a DTPA-cs124-Ln(III) chelate, a BHHCT-Ln(III) chelate, a BPTA-Ln(III) chelate or a BCPDA-Ln(III) chelate.

The emulsion formation step (S20) comprises: an oil-phase mixture preparation step of preparing an oil-phase mixture including cyclohexane, n-hexanol and a nonionic surfactant, a water-phase mixture preparation step of preparing a water-phase mixture including ammonium hydroxide and an aqueous solution containing the silane-lanthanide chelate complex, and a mixture formation step of forming a water-in-oil microemulsion by stirring the oil-phase mixture and the water-phase mixture.

The oil-phase mixture preparation step is preparing the oil-phase mixture by mixing 60 to 70 parts by weight of the cyclohexane, 10 to 20 parts by weight of the n-hexanol, and 15 to 25 parts by weight of the nonionic surfactant, based on 100 parts by weight of the oil-phase mixture.

The silica introduction step (S30) is introducing a silica precursor into the micelles by adding the microemulsion with 1 to 3 parts by weight of TEOS (tetraethyl orthosilicate) based on 100 parts by weight of the oil-phase mixture.

The nanoparticle synthesis step (S40) is performed in a manner in which the silica precursor introduced into the micelles is hydrolyzed through reaction for 20 to 30 hr, and is crosslinked with the silane-lanthanide chelate complex in the micelles to form silica seeds, which are then grown to thus synthesize fluorescent silica nanoparticles.

The nanoparticle synthesis step (S40) further comprises adjusting a size of the fluorescent silica nanoparticles by adding acetone to the microemulsion to break up the micelles (S40-1).

The method of the invention further comprises, after the nanoparticle synthesis step, a nanoparticle-obtaining step (S50) of obtaining fluorescent silica nanoparticles by, after termination of synthesis of the fluorescent silica nanoparticles, removing a supernatant using a centrifuge, performing washing using acetone and ethanol, and separating aggregated non-covalent particles using ultrasonic waves from a surfactant-added buffer.

In addition, the present invention provides lanthanide fluorescent silica nanoparticles, in which a silane-lanthanide chelate complex and a silica precursor are crosslinked or covalently bonded and are thus uniformly distributed in the particles and which have an average particle size (D50) of 50 to 150 nm and include a maximum absorption wavelength peak of 320 to 360 nm and a maximum emission wavelength peak of 650 to 700 nm upon fluorescence spectrum measurement in an aqueous solution. Also, an additional emission wavelength peak of 580 to 630 nm is further included.

The silane-lanthanide chelate complex is a complex configured such that a lanthanide chelate, a functional group having reactivity to an amine group or a thiol group, and a silane compound are linked to each other, and is preferably a silane-europium (Eu) chelate complex having a Stokes shift of 300 to 400 nm.

In addition, the present invention provides a fluorophore for fluorescence analysis, comprising the aforementioned lanthanide fluorescent silica nanoparticles.

Also, the fluorophore of the invention further comprises an antibody immobilized on the surface of the lanthanide fluorescent silica nanoparticles and is thus suitable for use in fluorescence analysis of a bio-derived material.

Advantageous Effects

According to the present invention, lanthanide fluorescent silica nanoparticles are manufactured by crosslinking a fluorescent probe, that is, a silane-lanthanide chelate, with a silica precursor, thereby providing lanthanide fluorescent silica nanoparticles (luminophore-encapsulated silica nanoparticles, LESNP) having improved fluorescence properties and chemical stability when applied to fluorescence analysis.

More particularly, a fluorescent probe complex and a silica structure are crosslinked and uniformly distributed in the particles, thereby solving problems with existing silica/polymer-based porous fluorescent nanoparticles, including loss of a fluorescent probe incorporated into pores of fluorescent nanoparticles to the outside of the particles. Furthermore, the fluorescent silica nanoparticles can enhance shielding effects against oxygen and water present in the external environment and can thus manifest excellent chemical stability.

Also, a method of manufacturing the fluorescent silica nanoparticles according to the present invention is a modification of typically useful preparation methods in the art, and can thus be applied without great changes to the construction of existing equipment for manufacturing silica nanoparticles.

Also, fluorescent silica nanoparticles obtained by the method of the present invention can exhibit fluorescence properties of a lanthanide used as the fluorescent probe and can thus be utilized in high-sensitivity fluorescence analysis of inorganic materials, bio-derived materials, or the like.

DESCRIPTION OF DRAWINGS

FIG. 1 is a flowchart showing a process of manufacturing lanthanide fluorescent silica nanoparticles according to an embodiment of the present invention;

FIG. 2 schematically shows a process of manufacturing fluorescent silica nanoparticles by crosslinking a silica precursor with a silane-lanthanide chelate complex according to an embodiment of the present invention;

FIG. 3 shows a complex synthesis step in the first process according to an embodiment of the present invention;

FIG. 4 shows a complex synthesis step in the second process according to an embodiment of the present invention;

FIGS. 5 and 6 schematically show the preparation of fluorescent silica nanoparticles according to an embodiment of the present invention;

FIGS. 7 and 8 are photographs showing control particles and fluorescent silica nanoparticles according to an embodiment of the present invention, washed using different washing solutions;

FIG. 9 is an image showing the fluorescent silica nanoparticles according to an embodiment of the present invention, observed through a fluorescence filter;

FIG. 10 shows a fluorescence spectrum of the fluorescent silica nanoparticles according to an embodiment of the present invention in an aqueous solution;

FIG. 11 shows an SEM image of fluorescent silica nanoparticles according to an embodiment of the present invention;

FIG. 12 shows a TEM image of fluorescent silica nanoparticles according to an embodiment of the present invention;

FIG. 13 schematically shows the formation of antibody-immobilized fluorescent silica nanoparticles according to an exemplary embodiment of the present invention; and FIG. 14 shows the results of fluorescence microscopy of silica particles after reaction with the capture antibody-formulated surface.

MODE FOR INVENTION

In the following description of the present invention, the terms used herein are merely intended to describe specific embodiments and are not to be construed as limiting the scope of the present invention, which is defined by the appended claims. Unless otherwise defined, all technical or scientific terms used herein have the same meanings as those typically understood by persons having ordinary knowledge in the art to which the present invention belongs.

Unless otherwise stated, the terms "comprise", "comprises" and "comprising" are used to designate the presence of an object, a step or groups of objects and steps described in the specification and claims, and should be understood as not excluding the presence or additional probability of any other objects, steps or groups of objects or steps.

Unless otherwise noted, various embodiments of the present invention may be combined with other embodiments. In particular, any feature which is mentioned preferably or favorably may be combined with any other features which may be mentioned preferably or favorably. Hereinafter, a description will be given of embodiments of the present invention and effects thereof with reference to the appended drawings.

<Method of Manufacturing Lanthanide Fluorescent Silica Nanoparticles>

According to an embodiment of the present invention, a method of manufacturing lanthanide fluorescent silica nanoparticles include a complex synthesis step (S10) of synthesizing a fluorescent probe complex, an emulsion formation step (S20) of forming a water-in-oil microemulsion in which micelles containing therein the fluorescent probe complex are dispersed, a silica introduction step (S30) of introducing a silica structure into the microemulsion, and a nanoparticle synthesis step (S40) of synthesizing fluorescent silica nanoparticles by crosslinking the fluorescent probe complex and the silica structure.

FIG. 1 is a flowchart showing the process of manufacturing lanthanide fluorescent silica nanoparticles according to an embodiment of the present invention, and FIG. 2 schematically shows the process of manufacturing fluorescent silica nanoparticles by crosslinking the silica precursor with the silane-lanthanide chelate complex according to an embodiment of the present invention.

In the present invention, the lanthanide fluorescent silica nanoparticles are manufactured by crosslinking a fluorescent probe, that is, a silane-lanthanide chelate, with a silica precursor, thereby providing lanthanide fluorescent silica nanoparticles (luminophore-encapsulated silica nanoparticles, LESNP) having improved fluorescence properties and chemical stability when applied to fluorescence analysis.

More specifically, the fluorescent probe complex and the silica structure are crosslinked and thus uniformly distributed in the particles, thus solving problems with existing silica/polymer-based porous fluorescent nanoparticles, including loss of a fluorescent probe incorporated into pores of fluorescent nanoparticles to the outside of the particles. The fluorescent silica nanoparticles may enhance shielding effects against oxygen and water present in the external environment and may thus exhibit excellent chemical stability.

In the present invention, a lanthanide element is used as the fluorescent probe, and a Stöber method, which is a water-in-oil (W/O) microemulsion process using nano-sized micelles, is performed. More specifically, the fluorescent probe complex containing a lanthanide element and a silane group is synthesized, and a water-in-oil microemulsion is formed, thereby manufacturing lanthanide fluorescent silica nanoparticles in which the fluorescent probe complex and the silica structure are covalently bonded through a crosslinking reaction in the micelles having a water-phase core and are uniformly distributed in the particles.

Below, the method of manufacturing the lanthanide fluorescent silica nanoparticles is described stepwise.

According to an embodiment of the present invention, the complex synthesis step (S10) is synthesizing a fluorescent probe complex, and particularly synthesizing a fluorescent probe complex, that is, a silane-lanthanide chelate complex. The complex synthesis step (S10) is formulating the fluorescent probe, that is, the lanthanide chelate, with a silane group, which may be performed through the first process or the second process.

The complex synthesis step of the first process may include a first complex synthesis step (S11-1) of synthesizing a cyanuric chloride-lanthanide chelate and a second complex synthesis step (S11-2) of synthesizing a silane-lanthanide chelate complex. FIG. 3 shows the complex synthesis step based on the first process according to an embodiment of the present invention.

The first complex synthesis step (S11-1) is synthesizing a cyanuric chloride-lanthanide chelate by adding and reacting a lanthanide chelate (*R) containing an amine group with cyanuric chloride, in which the lanthanide chelate is formulated with cyanuric chloride having specific reactivity to an amine group in the presence of acetone.

The lanthanide chelate (*R) containing an amine group is illustrated below.

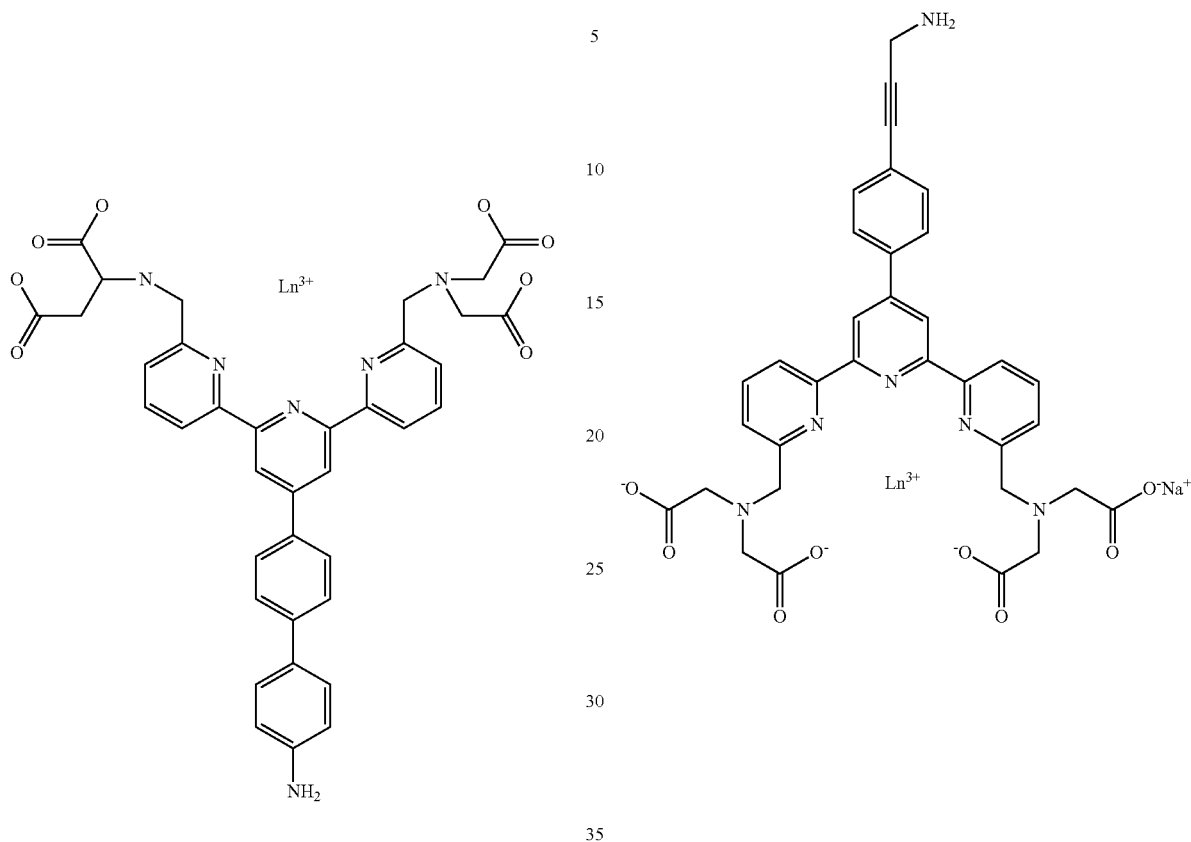

Furthermore, trisbipyridine (TBP) cryptate-$Ln^{3+}$, trimethyltryptamine (TMT)-$Ln^{3+}$, and the like may be used, but the present invention is not limited thereto, and various examples of the lanthanide chelate (*R) containing an amine group may be embodied.

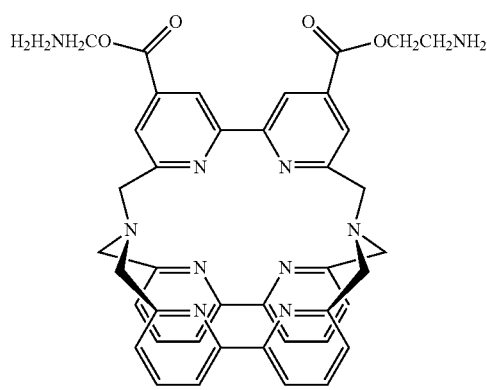

The second complex synthesis step (S11-2) is synthesizing a silane-lanthanide chelate complex by adding and reacting the cyanuric chloride-lanthanide chelate with aminosilane, and the chlorine group of a cyanuric structure attached to the cyanuric chloride-lanthanide chelate synthesized by the first complex synthesis step (S11-1) specifically reacts with the amine group of an aminosilane compound in a water phase, thus synthesizing a silane-lanthanide chelate complex, in which the lanthanide chelate-cyanuric structure-aminosilane are sequentially linked.

The complex synthesis step of the second process is synthesizing a silane-lanthanide chelate complex by adding and reacting a lanthanide chelate (*R) containing a residue (*X) having reactivity to an amine group or a thiol group with a silane compound having an amine group or a thiol group. FIG. 4 shows the complex synthesis step based on the second process according to an embodiment of the present invention. The lanthanide chelate (*R) is not limited to the lanthanide chelate (*R) shown in FIG. 4, and may include a lanthanide chelate (*R) shown below.

Examples of the lanthanide chelate (*R) according to an embodiment of the present invention may include a TBP-Ln(III) chelate, a DTPA-cs124-Ln(III) chelate, a BHHCT-Ln(III) chelate, a BPTA-Ln(III) chelate and a BCPDA-Ln(III) chelate, which are respectively illustrated below.

a) TBP-Ln(III) chelate (Lanthanide(III) trisbipyridine cryptate)

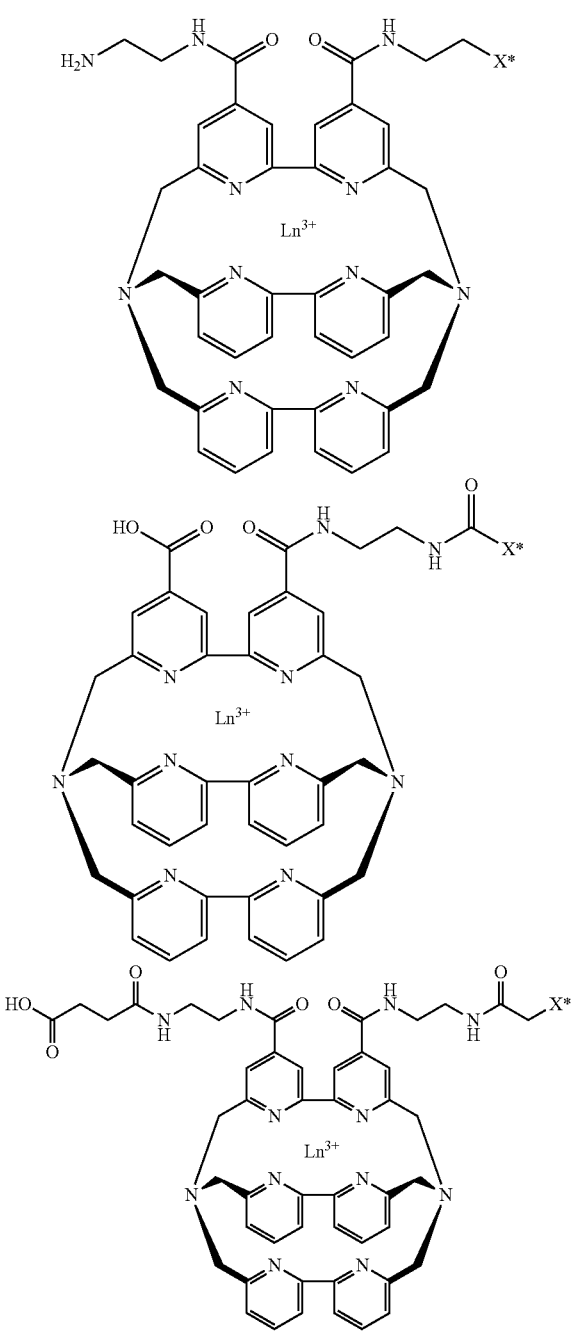

b) DTPA-cs124-Ln (III) chelate
   DTPA: diethylenetriaminepentaacetic acid dianhydride
   Cs124: 7-amino-4-methy-2-quinolone (Carbostyril 124)

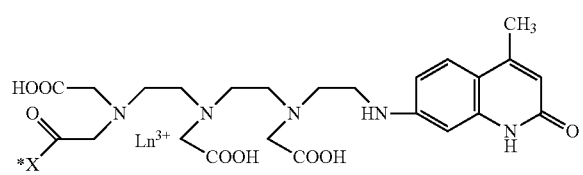

-continued

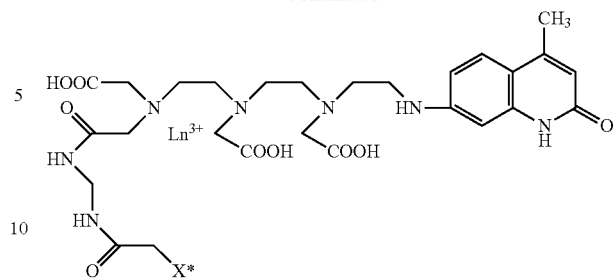

c) BHHCT-Ln(III) chelate
   BHHCT:
   3,4-bis[4-(4,4,5,5,6,6,6-heptafluoro-3-oxohexanoyl)phenyl]benzenesulfonyl chloride

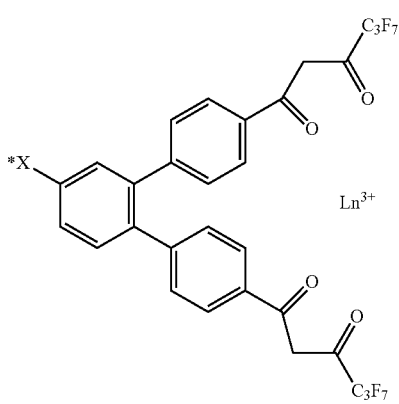

d) BPTA-Ln(III) chelate
   BPTA:
   N,N,N$_1$,N$_1$-[2,6-bis(3'-aminomethyl-1'-pyrazolyl)-4-phenylpyridine] tetrakis(acetic acid)

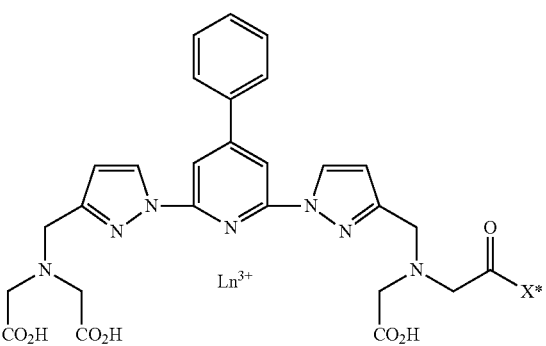

e) BCPDA-Ln(III) chelate
BCPDA: 4,7-bis(chlorosulfophenyl)-1,10-phenanthroline-2,9-dicarboxylic acid

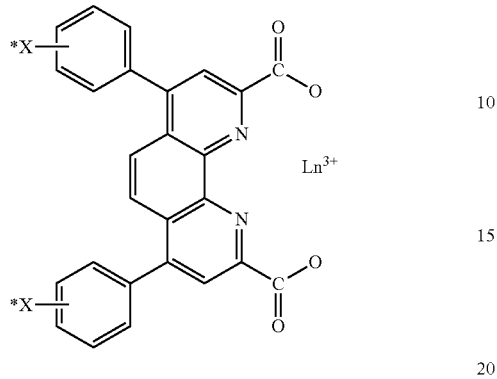

Also, the residue (*X) according to an embodiment of the present invention includes at least one functional group selected from the group consisting of carboxylate, N-hydroxysuccinimide, isothiocyanate, maleimide and sulfonyl chloride.

The lanthanide chelate (*R) containing the residue (*X) used in the complex synthesis step of the second process is illustrated below.

a)
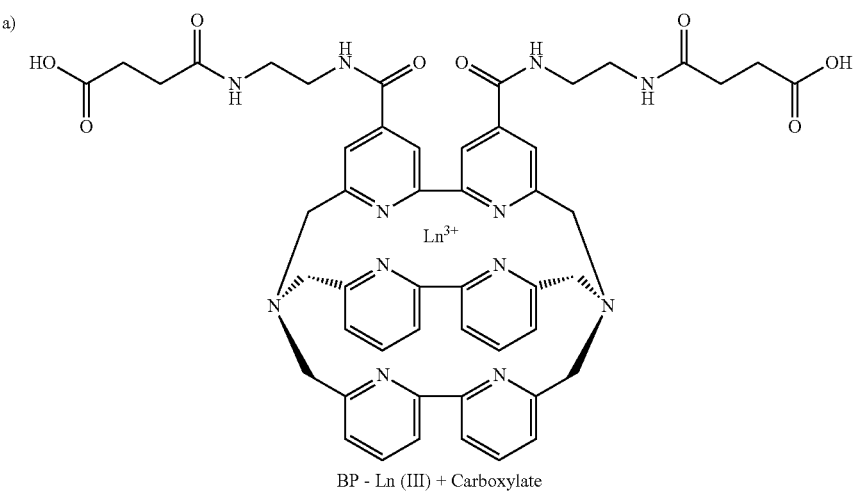
BP - Ln (III) + Carboxylate b)
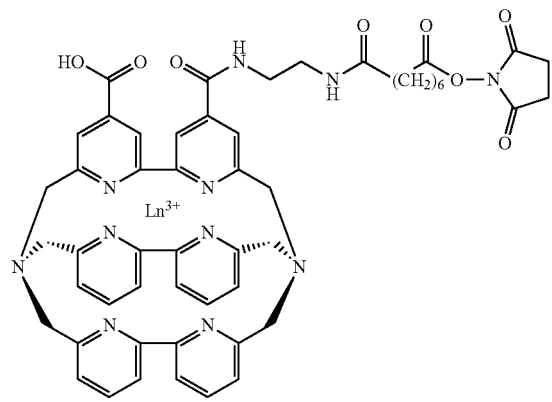
BP - Ln (III) + N-Hydroxysuccinimide c)
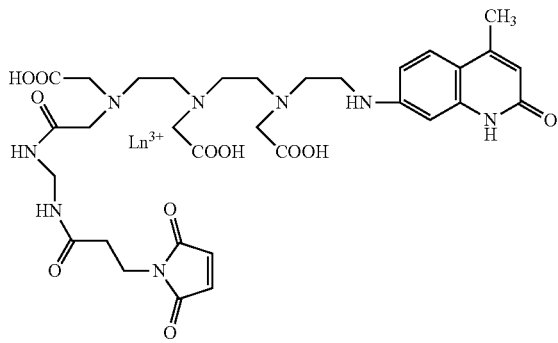
DTPA-cs124-Ln(III) + Maleimide -continued d) 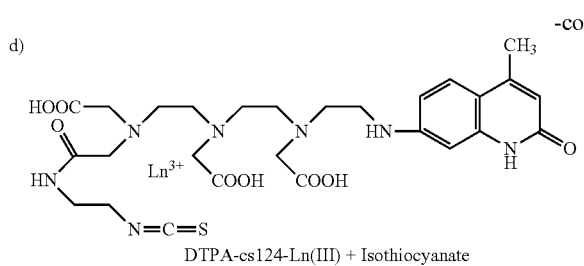
DTPA-cs124-Ln(III) + Isothiocyanate e) 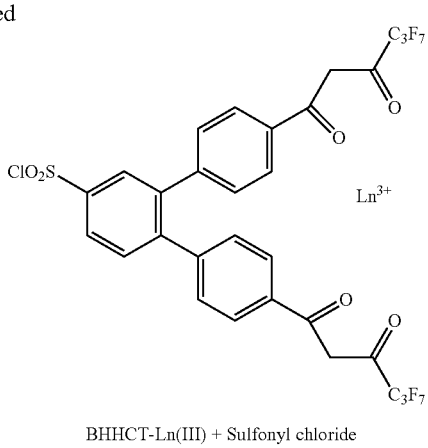
BHHCT-Ln(III) + Sulfonyl chloride f) 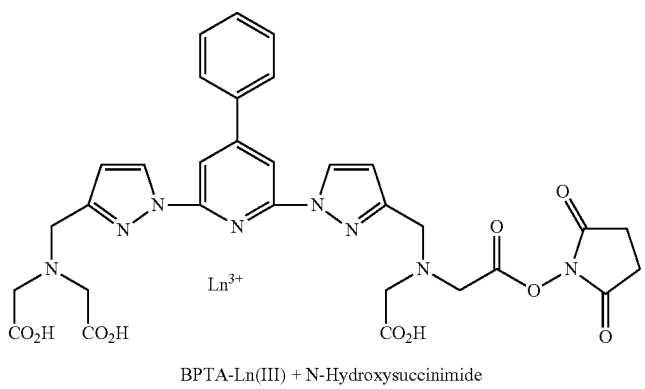
BPTA-Ln(III) + N-Hydroxysuccinimide The lanthanide element, which is usable in the complex synthesis step (S10) according to an embodiment of the present invention, may include at least one selected from the group consisting of europium (Eu), cerium (Ce), neodymium (Nd) and yttrium (Y). Preferably, europium (Eu) is used.

The emulsion formation step (S20) according to an embodiment of the present invention is forming a water-in-oil microemulsion in which micelles containing therein the fluorescent probe complex are dispersed, and particularly, the water-in-oil microemulsion is configured such that micelles, the water-phase core of which is introduced with the silane-lanthanide chelate complex synthesized by the complex synthesis step (S10), are dispersed in an oil-phase solvent.

In the micelles having the water-phase core of the formed water-in-oil microemulsion, hydrolysis and condensation of a silica precursor, which will be introduced later, occur.

The emulsion formation step (S20) includes an oil-phase mixture preparation step of preparing an oil-phase mixture, a water-phase mixture preparation step of preparing a water-phase mixture, and a mixture formation step of forming a water-in-oil microemulsion.

The oil-phase mixture preparation step is preparing an oil-phase mixture including cyclohexane, n-hexanol and a nonionic surfactant by mixing materials that constitute the oil-phase mixture at a specific ratio.

The mixing ratio of the materials for the oil-phase mixture is as follows: based on 100 parts by weight of the oil-phase mixture, 60 to 70 parts by weight of cyclohexane, 10 to 20 parts by weight of n-hexanol, and 15 to 25 parts by weight of a nonionic surfactant.

The amount of the nonionic surfactant affects the rigidity of the micelles in the formed microemulsion, and has an influence on the extent to which the silica precursor dispersed in the oil-phase solvent penetrates into the water-phase micelle core and is thus hydrolyzed in the silica introduction step (S30).

The nonionic surfactant preferably includes a Triton-based surfactant, such as polyoxyethylene-p-octylphenyl ether, etc. Examples thereof include Triton X-100, Triton X-45, Triton X-114, Triton X-102, Triton X-165, Triton X-305, Triton X-405, and Nonider P-40, and Triton X-100 is preferably used.

The water-phase mixture preparation step is preparing a water-phase mixture including ammonium hydroxide and an aqueous solution containing the silane-lanthanide chelate complex prepared by the complex synthesis step (S10) by mixing the materials for the water-phase mixture at a specific ratio. Ammonium hydroxide is a material that catalyzes hydrolysis of the silica structure that is added, and is contained in an amount of 5 to 10 parts by weight based on 100 parts by weight of the water-phase mixture.

The mixture formation step is forming a water-in-oil microemulsion by stirring the oil-phase mixture prepared by the oil-phase mixture preparation step and the water-phase mixture prepared by the water-phase mixture preparation step. The oil-phase mixture and the water-phase mixture are stirred for 20 to 60 min, thus forming nano-sized micelles to thereby obtain a water-in-oil microemulsion in which the micelles having the water-phase core are dispersed in the oil-phase solvent.

In the mixture formation step, the oil-phase mixture and the water-phase mixture are mixed at a weight ratio of 100:6 to 7.

The microemulsion formed by the emulsion formation step (S20) is configured such that the micelles having the water-phase core are dispersed in the oil-phase solvent containing the surfactant, in which the micelle size is about hundreds of nm. Each micelle is a nano-scale reactor in which a Stöber reaction occurs, thereby synthesizing silica nanoparticles.

The silica introduction step (S30) according to an embodiment of the present invention is introducing a silica structure to the microemulsion, and particularly introducing a silica precursor to the microemulsion formed in the emulsion formation step (S20).

The silica introduction step (S30) is introducing the silica precursor into the micelles by adding the microemulsion formed by the emulsion formation step (S20) with TEOS (tetraethyl orthosilicate).

The silica introduction step (S30) is adding 1 to 3 parts by weight of the silica precursor based on 100 parts by weight of the oil-phase mixture. The amount of the silica precursor that is added affects the size of the particles, and is set to the above range in order to prevent parasite nucleation, which interferes with proper particle formation.

The nanoparticle synthesis step (S40) according to an embodiment of the present invention is synthesizing fluorescent silica nanoparticles by crosslinking the fluorescent probe complex and the silica structure, and particularly, the silica precursor introduced by the silica introduction step (S30) is crosslinked with the silane-lanthanide chelate complex in the micelles, thus synthesizing fluorescent silica nanoparticles.

In the nanoparticle synthesis step (S40), the silica precursor introduced into the micelles is hydrolyzed, and is crosslinked with the silane-lanthanide chelate complex in the micelles to form silica seeds, and the silica seeds thus formed are continuously grown to thus synthesize fluorescent silica nanoparticles.

The reaction time for synthesis of nanoparticles determines the size of particles, and the nanoparticle synthesis step (S40) according to the present invention is synthesizing fluorescent silica nanoparticles through reaction for 20 to 30 hr. The silica precursor present in the oil phase penetrates into the micelles, whereby nucleation of silica particles occurs in the water-phase micelle reactors, after which hydrolysis and condensation of the silica precursor occur around the silica seeds, whereby the particles are grown.

The nanoparticle synthesis step (S40) according to an embodiment of the present invention further includes a particle size control step (S40-1) of adjusting the size of the fluorescent silica nanoparticles.

The particle size control step (S40-1) is adjusting the size of the fluorescent silica nanoparticles by breaking up the micelles by adding an excess of acetone to the microemulsion in which the fluorescent silica nanoparticles are grown.

The reaction time, the amount of surfactant, the amount of added silica precursor and the size of particles are correlated with each other, and have to be optimized in order to obtain particles having a desired size.

The method of manufacturing the lanthanide fluorescent silica nanoparticles according to an embodiment of the present invention further includes a nanoparticle-obtaining step (S50). After the nanoparticle synthesis step (S40), that is, after termination of synthesis of the fluorescent silica nanoparticles, the nanoparticle-obtaining step (S50) includes removing a supernatant using a centrifuge (S51), performing washing three times or more using acetone and ethanol (S52), and then separating aggregated non-covalent particles using ultrasonic waves from the surfactant-added buffer (S53), thereby obtaining fluorescent silica nanoparticles.

For example, upon washing (S52), first washing using a mixed solution comprising acetone and ethanol at a ratio of 1:0.8 to 1.2, second washing using an ethanol solution, and third washing using a surfactant solution (e.g. Tween 20) may be performed using a centrifuge.

Unlike conventional amorphous silica particles having the high likelihood of loss of the fluorescent probe to the outside of the particles due to the porous structure thereof, the fluorescent silica nanoparticles obtained by the method of the present invention are remarkably decreased in likelihood of loss of the fluorescent probe to the outside of the particles by virtue of covalent bonding of the internally incorporated fluorescent probe with the silica structure, and may enhance shielding effects against oxygen and water present in the external environment, thus exhibiting superior chemical stability. By virtue of such structural features, problems of loss of the internal material in the conventional fluorescent silica particles and chemical instability problems thereof may be overcome.

Also, the method of manufacturing the fluorescent silica nanoparticles according to the present invention is a modification of typically useful preparation methods in the art, and may be favorably applied without great changes in the construction of existing equipment for manufacturing silica nanoparticles.

Also, the fluorescent silica nanoparticles obtained by the method of the present invention may exhibit fluorescence properties of the lanthanide used as the fluorescent probe, whereby high-sensitivity fluorescence analysis becomes possible.

<Lanthanide Fluorescent Silica Nanoparticles>

The lanthanide fluorescent silica nanoparticles according to an embodiment of the present invention are nanoparticles formed by crosslinking a lanthanide fluorescent probe complex and a silica structure, and are more particularly lanthanide fluorescent silica nanoparticles in which a silane-lanthanide chelate complex and a silica structure are crosslinked or covalently bonded and are thus uniformly distributed in the particles.

The silane-lanthanide chelate complex, which is structurally contained in the lanthanide fluorescent silica nanoparticles according to the present invention, is a complex configured such that a lanthanide chelate, a functional group having reactivity to an amine group or a thiol group and a silane compound are linked to each other.

The lanthanide chelate, which is structurally contained in the silane-lanthanide chelate complex, is a lanthanide chelate including a TBP-Ln(III) chelate, a DTPA-cs124-Ln(III) chelate, a BHHCT-Ln(III) chelate, a BPTA-Ln(III) chelate or a BCPDA-Ln(III) chelate.

The functional group having reactivity to an amine group or a thiol group, which is structurally contained in the silane-lanthanide chelate complex, is at least one functional group selected from the group consisting of carboxylate, N-hydroxysuccinimide, isothiocyanate, maleimide and sulfonyl chloride.

The lanthanide fluorescent silica nanoparticles according to an embodiment of the present invention have an average particle size (D50) of 50 to 150 nm. Upon preparation of the lanthanide fluorescent silica nanoparticles, the average particle size may be controlled by adjusting the reaction time, the amount of surfactant and the amount of added silica precursor, and lanthanide fluorescent silica nanoparticles having various sizes ranging from tens of nm to hundreds of nm may be employed depending on the end use.

Also, the lanthanide fluorescent silica nanoparticles according to an embodiment of the present invention have a Stokes shift of 300 to 400 nm. Furthermore, the lanthanide fluorescent silica nanoparticles according to an embodiment of the present invention show a maximum absorption wavelength peak of 320 to 360 nm and a maximum emission wavelength peak of 650 to 700 nm upon measurement of a fluorescence spectrum in an aqueous solution.

Furthermore, the lanthanide fluorescent silica nanoparticles show an additional emission wavelength peak of 580 to 630 nm, and the signal intensity thereof is very stable compared to the maximum emission wavelength peak.

EXAMPLES

Fluorescent silica nanoparticles were manufactured by introducing a silane-europium chelate complex using a europium ($Eu^{3+}$) chelate among fluorescent lanthanide chelates. Here, the lanthanide chelate used as the fluorescent probe of the fluorescent silica nanoparticles was sodium [4'-(4'-amino-4-biphenylyl)-2,2':6',2"-terpyridine-6,6"-diylbis(methyliminodiacetato)]europate(III) (ATBTA-$Eu^{3+}$), made by and purchased from TCI. With reference to FIGS. 5 and 6, specific examples are described below.

In order to synthesize a complex (a silane-lanthanide chelate complex) of a europium chelate and an aminosilane compound, an amine group exposed to the end of ATBTA-$Eu^{3+}$ was reacted with cyanuric chloride in the presence of acetone, thus preparing a cyanuric chloride-europium chelate (DTBTA-$Eu^{3+}$) in which two chlorine groups able to covalently bind to another amine group are exposed. The cyanuric chloride-europium chelate thus synthesized is {{2,2',2''',2'''-{4'-{[(4,6-dichloro-1,3,5-triazin-2-yl)amino]biphenyl-4-yl}-2,2':6',2"-diyl}bis-(methylenenitrilo)}tetrakis(acetato)}europium(III) (DTBTA-$Eu^{3+}$), and the terminal functional group may covalently bind to the amine group.

Then, DTBTA-$Eu^{3+}$, which is the synthesized cyanuric chloride-europium chelate, was reacted with an aminosilane compound (3-aminopropyl)triethoxysilane (APTES), and the two compounds were reacted at an equivalent mol ratio of 1:4 in a 10 mM bicarbonate buffer at room temperature for 2 hr, thus synthesizing a silane-europium complex, DTBTA-$Eu^{3+}$/APTES.

Then, in order to form a water-in-oil reverse microemulsion, cyclohexane, 1-hexanol and Triton X-100 were mixed at a volume ratio of 4:1:1 to give 5 g of an oil-phase solution, which was then added with 35 mg of an ammonium hydroxide solution and 295 mg of the DTBTA-$Eu^{3+}$/APTES aqueous solution and sufficiently dispersed, after which 800 mg of a silica precursor, tetraethyl orthosilicate (TEOS), was added thereto and sufficiently reacted with stirring for 24 hr.

The synthesized silane-europium chelate complex (DTBTA-$Eu^{3+}$/APTES) was added in a water phase into the microemulsion, and TEOS, as the silica precursor present in the oil phase, was made to penetrate into the water phase of the micelles, followed not only by hydrolysis and condensation but also by crosslinking with the europium chelate, thus synthesizing fluorescent silica nanoparticles in which the europium chelate was uniformly present in the particles.

To break up the microemulsion, an excess of acetone was added, and the particles were precipitated in the form of an aggregate on the bottom of a reaction vessel and the supernatant was removed, after which first washing using a washing solution comprising acetone and ethanol mixed at a ratio of 1:1, second washing using ethanol and third washing using a Tween 20 solution were performed through centrifugation, thus obtaining fluorescent silica nanoparticles.

The obtained fluorescent silica nanoparticles had an average particle size (D50) of 70 nm, and the fluorescence properties thereof were measured to have a maximum absorption wavelength of 342 nm and a maximum emission wavelength of 680 nm.

Test Examples (1) Dissolution of Fluorescent Probe

Whether the silane-lanthanide chelate complex, which is the fluorescent material in the fluorescent silica nanoparticles manufactured in Examples of the present invention, was dissolved was observed with the naked eye. Also, control particles containing the lanthanide chelate as the fluorescent material were used.

FIG. 7 shows photographs of control particles washed using different washing solutions, and FIG. 8 shows photographs of fluorescent silica nanoparticles according to an embodiment of the present invention, washed using different washing solutions.

When the control particles were washed with a mixed solution of ethanol and acetone, as shown in FIG. 7, the fluorescent material was dissolved in a large amount, and the supernatant became opaque even upon washing with ethanol or a surfactant, indicating that dissolution occurred to some extent. In contrast, in the fluorescent silica nanoparticles shown in FIG. 8, the fluorescent probe was not dissolved regardless of the kind of washing solution.

(2) Fluorescence Microscopy

The fluorescent silica nanoparticles, manufactured according to an embodiment of the present invention, were observed through a fluorescence filter having an excitation wavelength of 340 nm and an emission wavelength of 615 to 625 nm using a fluorescence microscope. FIG. 9 shows the image of fluorescent silica nanoparticles according to an embodiment of the present invention, observed through a fluorescence filter.

Upon observation of a fluorescence signal using a fluorescence filter based on excitation and emission wavelength properties of a lanthanide material, the fluorescence signal of auto-fluorescence occurring from bio-derived materials was blocked, and thus it was possible to selectively obtain the fluorescence signal only of the synthesized fluorescent particles.

(3) Fluorescence Spectrum Analysis

The fluorescence spectrum of the fluorescent silica nanoparticles according to an embodiment of the present invention in an aqueous solution was analyzed using a fluorescence spectrometer. FIG. 10 shows the fluorescence spectrum of the fluorescent silica nanoparticles according to an embodiment of the present invention in the presence of an aqueous solution.

As results thereof, the maximum absorption wavelength was measured to be 342 nm and the maximum emission wavelength was observed to be 680 nm, and thus a wide Stokes shift was exhibited. Additionally, the emission points of various wavelength bands were observed due to the fluorescence properties of the lanthanide element, and in particular, an additional emission wavelength peak was observed at 610 to 620 nm, which is the maximum emission wavelength of ATBTA-$Eu^{3+}$. The ratio of the intensity of the additional emission wavelength peak relative to the intensity of the maximum emission wavelength peak was 0.6 to 0.7.

Thereby, it can be confirmed that the intrinsic fluorescence properties of the lanthanide chelate (ATBTA-$Eu^{3+}$) in the particles obtained through crosslinking with the silica structure did not change greatly.

(4) Scanning Electron Microscopy (SEM)

The SEM image of the fluorescent silica nanoparticles according to an embodiment of the present invention is shown in FIG. 11. An image on a scale of hundreds of nm was obtained through SEM. Based on the image analysis, it can be confirmed that the manufactured nanoparticles had a uniform size of about 60 to 70 nm and were spherical.

(5) Transmission Electron Microscopy (TEM)

The TEM image of the fluorescent silica nanoparticles according to an embodiment of the present invention is shown in FIG. 12. The transmission image of the inside of the particles was obtained through TEM. Based on the image analysis, it can be confirmed that a certain component was not agglomerated at a predetermined portion in the silica particles but was uniform in the particles.

Based on the above analysis results, it can be concluded that the manufactured fluorescent silica nanoparticles exhibited lanthanide fluorescence properties and were present in the form of a sphere having a uniform size of tens of nm, and also that the silane-europium chelate complex used as the fluorescent probe was uniformly crosslinked in the particles.

<Application>

In order to verify the applicability of the fluorescent silica nanoparticles according to an embodiment of the present invention to the field of diagnosis of a bio-derived material, antibody immobilization was performed on the surface of the particles. In order to immobilize an antibody, a functional group targeting an amine group exposed on the antibody was exposed to the surface of the particles to thus bind to a desired antibody. FIG. 13 schematically shows the process of forming antibody-immobilized fluorescent silica nanoparticles according to an exemplary embodiment of the present invention.

The antibody-immobilized fluorescent particles, typically used to obtain a signal of a target material in fluorescence analysis, were formed through the following two steps. Also, in order to evaluate whether the antibody was successfully immobilized on the particles, control particles, in which an antibody-targeting functional group exposed to the surface of the particles was blocked, were formed.

Below, the antibody immobilization process through surface modification of the fluorescent silica nanoparticles and the method of verifying the antibody immobilization are described in detail.

(1) Step 1

Step 1 is modifying the surface of fluorescent silica nanoparticles to formulate the surface with a functional group having specific reactivity to an antibody. First, fluorescent silica nanoparticles were reacted with APTES and thus an amine group on the surface of the particles was exposed (step 1-1). Next, the particles having the exposed amine group were reacted with succinic anhydride having specific reactivity to an amine group, thus exposing a carboxyl group (step 1-2). Finally, in order to attach an n-hydroxysuccinimide (NHS) group targeting an amine of the antibody, the exposed carboxyl group was reacted with 1-ethyl-3-(3-dimethylaminopropyl)-carbodiimide hydrochloride (EDC), and then with n-hydroxysulfosuccinimide (sulfo-NHS) as a functional group targeting the antibody (step 1-3).

(2) Step 2

Step 2 is immobilizing the antibody by reacting the antibody with the antibody-targeting functional group (NHS group) exposed to the surface of the fluorescent silica nanoparticles. The antibody used was an anti-cTnI antibody (derived from a mouse) having reactivity to a cTnI protein used as a diagnostic marker for myocardial infarction.

(3) Formation of Control Particles

In order to verify whether antibody immobilization was realized on the fluorescent silica nanoparticles according to the present invention, a control was formed. The control particles were formed by blocking the NHS group with ethanolamine and bovine serum albumin (BSA) in lieu of the antibody as shown in ②-1 of FIG. 13.

(4) Verification of Antibody Immobilization

In order to verify whether antibody immobilization was realized on the finally obtained fluorescent silica nanoparticles, a DTSSP (3,3'-dithiobis[sulfosuccinimidylpropionate]) monolayer was formed on a gold sample, and a capture antibody (anti-mouse IgG antibody, from a goat), having specific reactivity to the antibody (anti-cTnI antibody, from a mouse) immobilized on the fluorescent silica nanoparticles, was immobilized on the DTSSP monolayer, and the extent of attachment of the particles to the gold sample was observed with a fluorescence microscope.

FIG. 14 shows the results of fluorescence microscopy of two kinds of particles after reaction with the capture antibody-formulated surface. Based on the test results, as shown in FIG. 14, when the control particles, formed by blocking the NHS group exposed to the particles in lieu of the antibody, were made to react with the capture antibody-immobilized gold surface, the fluorescence signal was not confirmed. In the antibody-immobilized particles, however, the fluorescence signal was observed by reacting many fluorescent particles with the capture antibody of the gold surface.

Thereby, as shown in the schematic view of FIG. 14, the particles that were not formulated with the antibody did not react with the capture antibody, and thus most of them were washed off during the washing process. On the other hand, the antibody-formulated particles were present in the form of being bound to the capture antibody even after the washing process through the reaction of the capture antibody with the antibody of the particles, whereby the fluorescence signal of the particles appeared upon fluorescence microscopy. Therefore, it can be concluded that the antibody was successfully immobilized on the surface of the manufactured fluorescent particles.

The fluorescent silica nanoparticles according to the present invention can be formulated with the functional group responsible for various reactions through surface modification, like conventional silica particles, and can also be formulated with the antibody having reactivity to a target material, whereby the particles of the invention can be very effectively employed in fluorescence assay for analysis of bio-derived materials.

The features, structures, effects and so on illustrated in individual exemplary embodiments as above may be combined or modified with other exemplary embodiments by those skilled in the art. Therefore, content related to such combinations or modifications should be understood to fall within the scope of the present invention.

The invention claimed is:

1. A method of manufacturing lanthanide fluorescent silica nanoparticles, comprising:
   a complex synthesis step of synthesizing a silane-lanthanide chelate complex;
   an emulsion formation step of forming a water-in-oil microemulsion by introducing the silane-lanthanide chelate complex into micelles having a water-phase core and dispersing the micelles containing therein the silane-lanthanide chelate complex in an oil-phase solvent;
a silica introduction step of introducing a silica precursor into the microemulsion; and
a nanoparticle synthesis step of synthesizing fluorescent silica nanoparticles by crosslinking the silica precursor and the silane-lanthanide chelate complex in the micelles,
wherein the complex synthesis step comprises:
a first complex synthesis step of synthesizing a cyanuric chloride-lanthanide chelate by adding and reacting a lanthanide chelate (*R) containing an amine group with cyanuric chloride, and
a second complex synthesis step of synthesizing a silane-lanthanide chelate complex by adding and reacting the cyanuric chloride-lanthanide chelate with aminosilane.

2. The method of claim 1, wherein the nanoparticle synthesis step is performed in a manner in which the silica precursor introduced into the micelles is hydrolyzed and is crosslinked with the silane-lanthanide chelate complex in the micelles to form silica seeds, which are then grown to thus synthesize fluorescent silica nanoparticles.

3. The method of claim 2, wherein the nanoparticle synthesis step is synthesizing the fluorescent silica nanoparticles through reaction for 20 to 30 hr.

4. A method of manufacturing lanthanide fluorescent silica nanoparticles, comprising:
a complex synthesis step of synthesizing a silane-lanthanide chelate complex;
an emulsion formation step of forming a water-in-oil microemulsion by introducing the silane-lanthanide chelate complex into micelles having a water-phase core and dispersing the micelles containing therein the silane-lanthanide chelate complex in an oil-phase solvent;
a silica introduction step of introducing a silica precursor into the microemulsion; and
a nanoparticle synthesis step of synthesizing fluorescent silica nanoparticles by crosslinking the silica precursor and the silane-lanthanide chelate complex in the micelles,
wherein the emulsion formation step comprises:
an oil-phase mixture preparation step of preparing an oil-phase mixture including cyclohexane, n-hexanol and a nonionic surfactant,
a water-phase mixture preparation step of preparing a water-phase mixture including ammonium hydroxide and an aqueous solution containing the silane-lanthanide chelate complex, and
a mixture formation step of forming a water-in-oil microemulsion by stirring the oil-phase mixture and the water-phase mixture.

5. The method of claim 4, wherein the oil-phase mixture preparation step is preparing the oil-phase mixture by mixing 60 to 70 parts by weight of the cyclohexane, 10 to 20 parts by weight of the n-hexanol, and 15 to 25 parts by weight of the nonionic surfactant, based on 100 parts by weight of the oil-phase mixture.

6. The method of claim 4, wherein the silica introduction step is introducing a silica precursor into the micelles by adding the microemulsion with TEOS (tetraethyl orthosilicate).

7. The method of claim 6, wherein, in the silica introduction step, the TEOS is added in an amount of 1 to 3 parts by weight based on 100 parts by weight of the oil-phase mixture.

8. A method of manufacturing lanthanide fluorescent silica nanoparticles, comprising:
a complex synthesis step of synthesizing a silane-lanthanide chelate complex;
an emulsion formation step of forming a water-in-oil microemulsion by introducing the silane-lanthanide chelate complex into micelles having a water-phase core and dispersing the micelles containing therein the silane-lanthanide chelate complex in an oil-phase solvent;
a silica introduction step of introducing a silica precursor into the microemulsion; and
a nanoparticle synthesis step of synthesizing fluorescent silica nanoparticles by crosslinking the silica precursor and the silane-lanthanide chelate complex in the micelles,
wherein the nanoparticle synthesis step is performed in a manner in which the silica precursor introduced into the micelles is hydrolyzed and is crosslinked with the silane-lanthanide chelate complex in the micelles to form silica seeds, which are then grown to thus synthesize fluorescent silica nanoparticles, and
wherein the nanoparticle synthesis step further comprises adjusting a size of the fluorescent silica nanoparticles by adding acetone to the microemulsion to break up the micelles.

9. A method of manufacturing lanthanide fluorescent silica nanoparticles, comprising:
a complex synthesis step of synthesizing a silane-lanthanide chelate complex;
an emulsion formation step of forming a water-in-oil microemulsion by introducing the silane-lanthanide chelate complex into micelles having a water-phase core and dispersing the micelles containing therein the silane-lanthanide chelate complex in an oil-phase solvent;
a silica introduction step of introducing a silica precursor into the microemulsion;
a nanoparticle synthesis step of synthesizing fluorescent silica nanoparticles by crosslinking the silica precursor and the silane-lanthanide chelate complex in the micelles, and
a nanoparticle-obtaining step of obtaining fluorescent silica nanoparticles by, after termination of synthesis of the fluorescent silica nanoparticles, removing a supernatant using a centrifuge, performing washing using acetone and ethanol, and separating aggregated non-covalent particles using ultrasonic waves from a surfactant-added buffer.

10. Lanthanide fluorescent silica nanoparticles, formed by crosslinking a silane-lanthanide chelate complex and a silica precursor,
wherein the silane-lanthanide chelate complex is a silane-europium (Eu) chelate complex, and the lanthanide fluorescent silica nanoparticles have a Stokes shift of 300 to 400 nm,
wherein the lanthanide fluorescent silica nanoparticles include a maximum absorption wavelength peak of 320 to 360 nm and a maximum emission wavelength peak of 650 to 700 nm upon fluorescence spectrum measurement in an aqueous solution, and
wherein the lanthanide fluorescent silica nanoparticles further include an additional emission wavelength peak of 580 to 630 nm upon fluorescence spectrum measurement in an aqueous solution.

11. The lanthanide fluorescent silica nanoparticles of claim 10, wherein the lanthanide fluorescent silica nanoparticles are configured such that the silane-lanthanide chelate complex and the silica structure are covalently bonded and are uniformly distributed in the particles.

12. The lanthanide fluorescent silica nanoparticles of claim 11, wherein the lanthanide fluorescent silica nanoparticles have an average particle size (D50) of 50 to 150 nm.

13. The lanthanide fluorescent silica nanoparticles of claim 10, wherein the silane-lanthanide chelate complex is a complex configured such that a lanthanide chelate, a functional group having reactivity to an amine group or a thiol group, and a silane compound are linked to each other.

14. The lanthanide fluorescent silica nanoparticles of claim 13, wherein the lanthanide chelate includes a TBP-Ln (III) chelate, a DTPA-cs124-Ln (III) chelate, a BHHCT-Ln (III) chelate, a BPTA-Ln (III) chelate or a BCPDA-Ln (III) chelate.

15. The lanthanide fluorescent silica nanoparticles of claim 13, wherein the functional group having reactivity to an amine group or a thiol group includes at least one functional group selected from the group consisting of carboxylate, N-hydroxysuccinimide, isothiocyanate, maleimide and sulfonyl chloride.

16. A fluorophore for fluorescence analysis, comprising the lanthanide fluorescent silica nanoparticles of claim 10.

17. The fluorophore of claim 16, wherein the fluorophore further comprises an antibody immobilized on a surface of the lanthanide fluorescent silica nanoparticles and is thus suitable for use in fluorescence analysis of a bio-derived material.

* * * * *